United States Patent
Ogut et al.

(10) Patent No.: US 10,441,470 B2
(45) Date of Patent: Oct. 15, 2019

(54) INTERACTIVE AIR PRESSURE EXCHANGE SYSTEM

(71) Applicants: Christopher E. Ogut, Portland, OR (US); Vitaliy Y. Gordeyev, Vancouver, WA (US)

(72) Inventors: Christopher E. Ogut, Portland, OR (US); Vitaliy Y. Gordeyev, Vancouver, WA (US)

(73) Assignee: 1964 Ears, LLC, Vancouver, WA (US)

( * ) Notice: Subject to any disclaimer, the term of this patent is extended or adjusted under 35 U.S.C. 154(b) by 271 days.

(21) Appl. No.: 15/425,881

(22) Filed: Feb. 6, 2017

(65) Prior Publication Data

US 2018/0221209 A1  Aug. 9, 2018

(51) Int. Cl.
 *A61F 11/08* (2006.01)
 *H04R 1/10* (2006.01)
 *H04R 25/00* (2006.01)

(52) U.S. Cl.
 CPC ............ *A61F 11/08* (2013.01); *H04R 1/1083* (2013.01); *A61F 2011/085* (2013.01); *A61F 2230/0069* (2013.01); *A61F 2240/002* (2013.01); *H04R 1/1016* (2013.01); *H04R 1/1091* (2013.01); *H04R 25/652* (2013.01); *H04R 2460/11* (2013.01)

(58) Field of Classification Search
 CPC .. H04R 1/1083; H04R 1/1091; H04R 1/1016; H04R 1/1058; H04R 1/2811; H04R 1/023; H04R 1/1075; H04R 1/2826; H04R 1/2849; H04R 1/2823; H04R 25/652; H04R 25/456; H04R 25/656; H04R 25/658; H04R 2460/11; H04R 2460/17; H04R 2460/15; H04R 2225/025; A61F 11/08; A61F 2011/085; A61F 2230/0069; A61F 2240/001; A61F 2240/002
 USPC .......................................... 381/380, 328, 373
 See application file for complete search history.

(56) References Cited

U.S. PATENT DOCUMENTS

| | | | | |
|---|---|---|---|---|
| 5,819,745 | A * | 10/1998 | Mobley | A61F 11/08 128/864 |
| 2009/0220113 | A1* | 9/2009 | Tiscareno | H04R 1/403 381/309 |
| 2017/0093079 | A1* | 3/2017 | Wagman | A45C 13/02 |

* cited by examiner

*Primary Examiner* — Yogeshkumar Patel
(74) *Attorney, Agent, or Firm* — Mersenne Law

(57) ABSTRACT

In-ear monitors, earphones and noise-attenuating earplugs are provided with a vent to improve insertion, removal and wearing comfort, and to protect delicate audio drivers from excessive pressure excursions. The vent is fitted with a pressure-management material such as a viscoelastic open-cell foam to control the rate at which air can pass through the vent. The pressure-management material permits tuning of the vent to achieve acoustically flat attenuation of ambient sound.

19 Claims, 5 Drawing Sheets

INTERACTIVE AIR PRESSURE EXCHANGE SYSTEM

CONTINUITY AND CLAIM OF PRIORITY

This is an original U.S. patent application.

FIELD

The invention relates to noise-suppression and audio-reproduction. More specifically, the invention relates to passive acoustic-wave modifying structures for inclusion in earplugs and earphones to improve insertion, wearing and removal comfort while maintaining favorable acoustic properties during use of the earplugs or earphones.

BACKGROUND

Many people rely on earplugs to protect their hearing from loud noises. In many applications, these devices merely need to reduce noise to a safe level, but some users are more demanding: the attenuated sound level should be acoustically "flat" (i.e., the relative levels of different audible frequencies should be similar to the original levels, but reduced across the entire sound spectrum for safety and comfort). This requirement is especially common among musicians and music technicians, who may play or work in a dangerously loud environment, but who still must be able to hear and judge the tonality of the sound.

Among these users, there is often the added requirement that another signal be added to the attenuated ambient sound. For example, a timing or "click" track, a previously-recorded audio track, or an amplified version of the user's own instrument or voice might be played directly into the user's ear, using a system of headphone audio drivers.

Earphones, also known as In-Ear Monitors ("IEMs") that fulfill these requirements are well-known. It is common for these to be crafted into a customized mold of the wearer's outer ear, and to extend somewhat into the ear canal. These devices seal well to the ear canal, so they are very effective to control and reduce the volume or amplitude of ambient sounds. Further, the portion that rests in the outer ear is large enough to contain one or more small headphone drivers, which can reproduce the additional sounds to be added to the ambient sound admitted through the IEMs. Such devices are also useful in quieter environments, where they serve as music- and sound-reproduction headphones that can reduce or block distracting environmental noise.

Because in-ear monitors and earplugs seal the ear canal, they create a small closed air volume with the eardrum (tympanic membrane) at one end. When the pressure in that volume is different from the pressure in the middle ear (which is more or less the same as ambient air pressure, mediated through the oral and nasal cavities and the Eustachian tube) it can cause discomfort during earplug insertion and removal, and "listening fatigue" during extended wear. However, adding a vent to equalize this pressure reduces the audio isolation and can disturb the desired acoustic balance.

Structures and methods to equalize ear-canal pressure without impairing audio balance may be of value in this field.

SUMMARY

Embodiments of the invention are earphones and earplugs that form a seal with the user's ear canal. A vent is provided to equalize pressures between the plugged ear canal and the ambient atmosphere outside the ear, but a pressure-management material such as a viscoelastic open-cell foam is placed in the vent to reduce or prevent impairment of the audio response of the earphones/earplugs by an open vent. In some embodiments, the pressure-management material is secured in a discrete, separable module to improve handling and performance, to offer adjustability of sound and/or isolation characteristics through a selection of compatible modules, and to obtain additional acoustic benefits.

DETAILED DESCRIPTION

Embodiments of the invention improve in-ear monitors and earplugs by providing a tuned pressure equalization vent to reduce or eliminate pressure differences between the wearer's plugged ear canal and external ambient air pressure. The vent increases insertion and removal comfort, offers reduced "listening fatigue" during use, and in high-performance monitors, can protect expensive audio drivers from damage due to over- and underpressure during insertion and removal.

Figure 1:
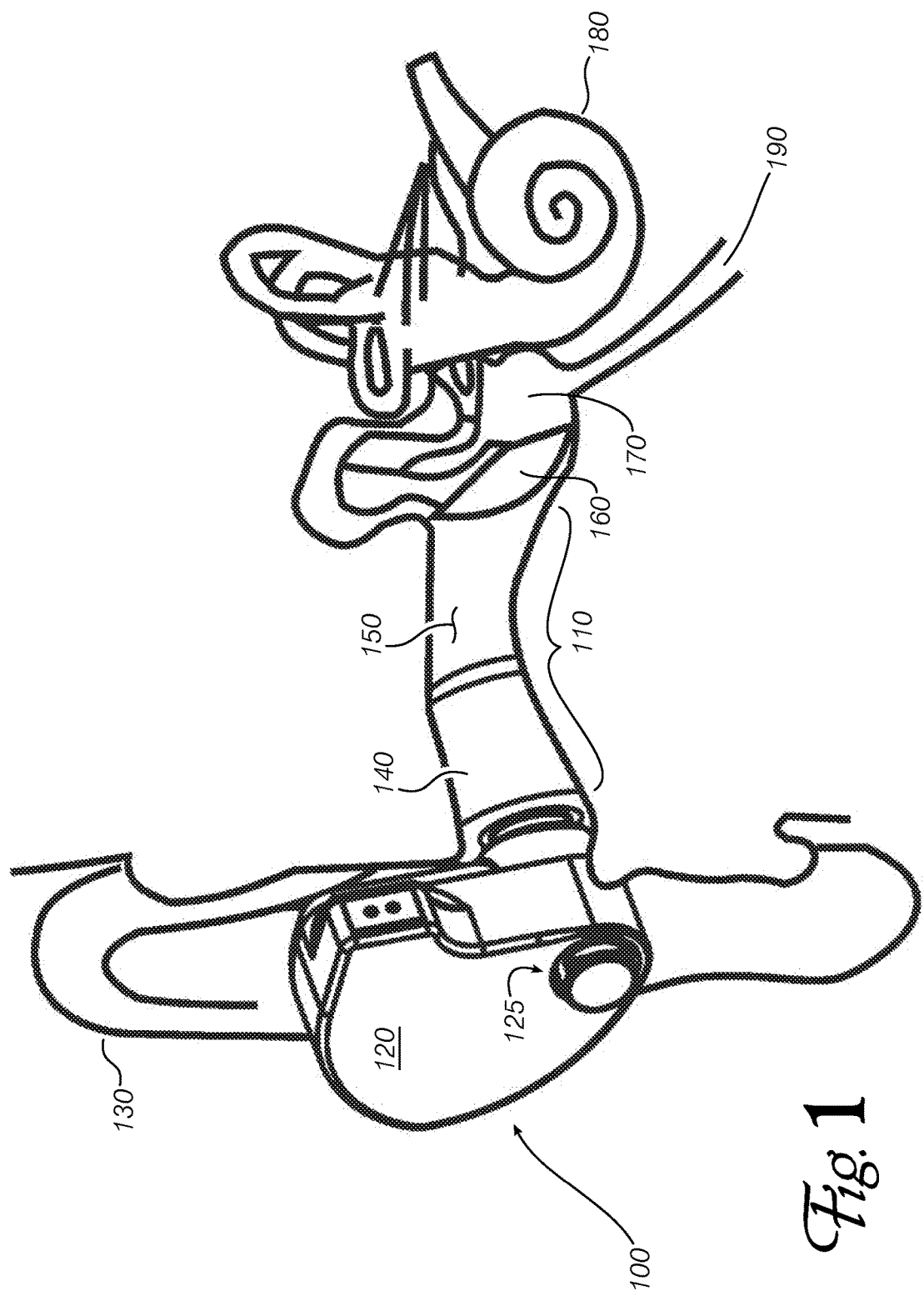
FIG. 1 shows a headphone according to an embodiment of the invention, inserted in a wearer's ear.

FIG. 1 shows a partial cutaway view of an in-ear monitor, generally 100, placed in a user's ear canal 110. The device comprises an outer portion 120 that rests in the user's outer ear 130. A molded stem or plug portion 140 fits into and seals the ear canal, creating a sealed space 150 between the plug 140 and the user's tympanic membrane ("eardrum") 160. On the other side of the eardrum, bones of the middle ear 170 transmit vibrations to the cochlea 180, where they are converted to neural signals and carried to the brain. The middle ear is maintained at roughly ambient pressure by air passing through the Eustachian tube 190 to the throat and sinuses (not shown).

Air pressure in the sealed space 150 is kept near the same ambient pressure by admitting or exhausting air through a tuned pressure equalization vent according to an embodiment. In this Figure, the outer portion of a modular vent component is visible at 125. Subsequent figures provide additional insight into the configuration and operation of the vent.

Figure 2:
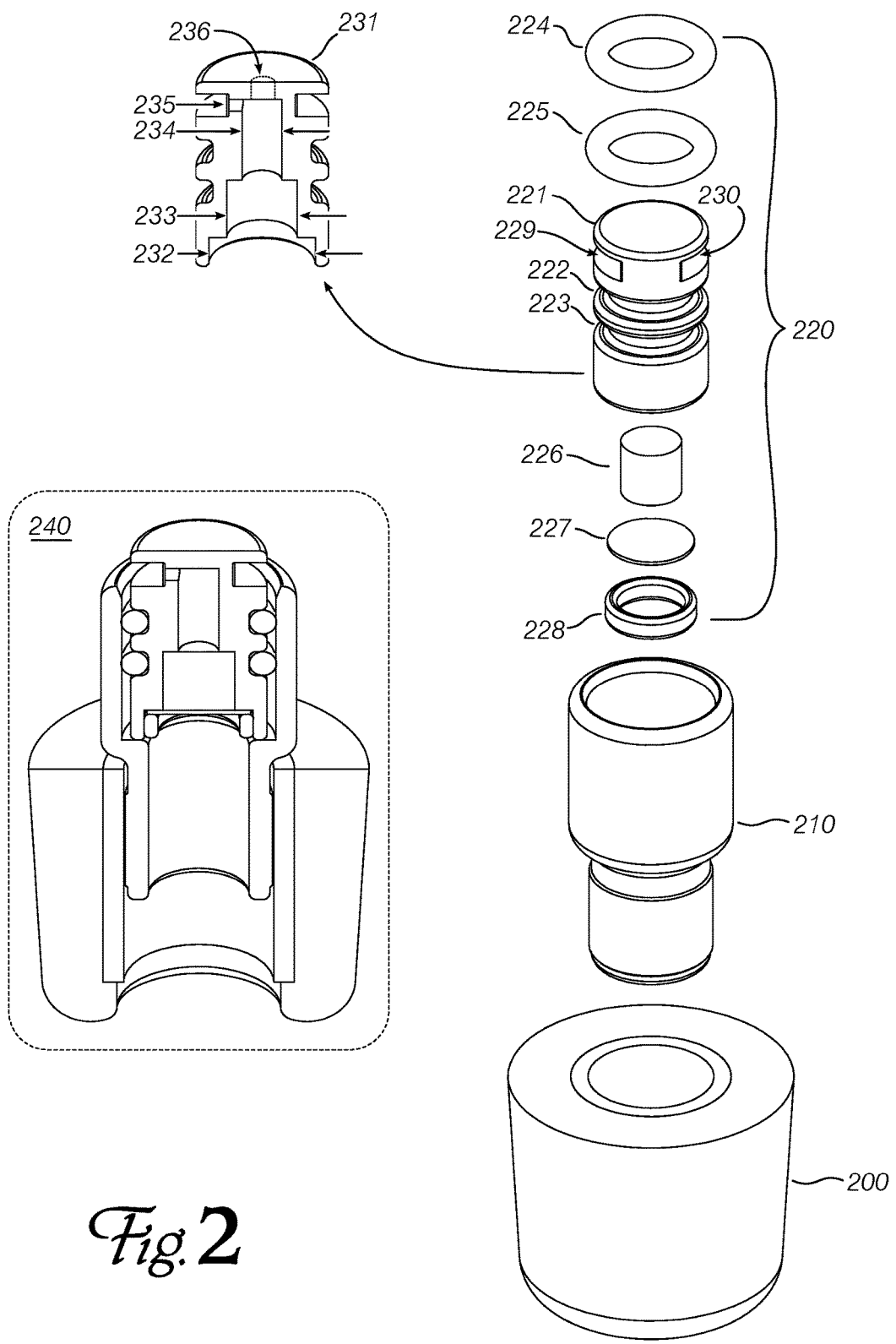
FIG. 2 shows an exploded and cutaway view of an embodiment that functions solely as a sound-reducing earplug.

FIG. 2 is an exploded view of an attenuating earplug (without audio reproduction capabilities) according to an embodiment of the invention. Element 200 is similar to element 140 in FIG. 1: it is a custom-molded or compressible plug that fits into and conforms to the walls of the user's ear canal. Element 210 is a socket—a hollow cylindrical structure that fits into plug 200. The socket permits air to flow freely through the plug even when it is inserted, so plug 200 and socket 210 alone offer very little noise attenuation.

Assembly 220 is an acoustically tuned vent module that fits into socket 210, substantially but not completely blocking the air channel through the socket. Vent module 220 comprises a main body 221, which may be cast, machined or otherwise formed from a rigid material such as plastic or metal. Cutaway 231 shows that the main body is partially hollow—it has three concentric holes of different diameters 232, 233, 234. The smallest and deepest hole 234 does not pass all the way through the body 231 (it is a "blind" hole), but an angled channel 235 does allow air to travel completely through the structure. (Channel 235 could be oriented coaxially with the other three holes and exit at 236, but the angled channel shown is preferable for reasons discussed below.)

Main body 221 comprises a plurality of exterior grooves or channels 222 and 223, which accept O-rings 224 and 225. These O-rings form a seal between assembly 220 and the interior of socket 210, preventing air from passing through the socket and assembly except by passing through the concentric holes 232, 233, 234 and angled channel 235.

An open-cell viscoelastic foam member 226 fits into hole 233, and a screen 227 and collet or retaining ring 228 hold foam member 226 in place. 227 and 228 are assembled into the largest concentric hole 232. Finally, main body 221 comprises slots 229 and 230. These slots are exposed when vent module 220 is fully inserted into socket 210. Inset 240 shows a cutaway view of the assembled configuration. The slots allow the vent module to be grasped by the user (e.g., by inserting his fingernails into the slots) and twisted to reorient the exit of the angled channel 235, or to extract the vent module 220 from socket 210 for disassembly and cleaning.

When the angled channel 235 exits from the side of the vent module, the outer orifice can be oriented at a preferred angle, regardless of the orientation of the assembled earplug in the user's ear canal. For example, if the vent module is rotated so that the angled channel 235 points backwards (towards the back of the user's head), it may reduce wind noise caused by air passing across the orifice when it is oriented in another direction.

The vent module permits air pressure to equalize by passing air through the concentric holes, screen, and particularly through the open-cell viscoelastic foam, which is principally responsible for controlling the air flow rate. Denser foam delays equalization, but improves ambient-noise attenuation. Less-dense foam permits faster pressure equalization, at the cost of reduced noise attenuation. Foam characteristics are preferably chosen to provide a flat audio response, then to achieve the desired attenuation level, and finally to permit swift pressure equalization. The tuning process described below may be followed to ensure suitable operational characteristics.

Figure 3:
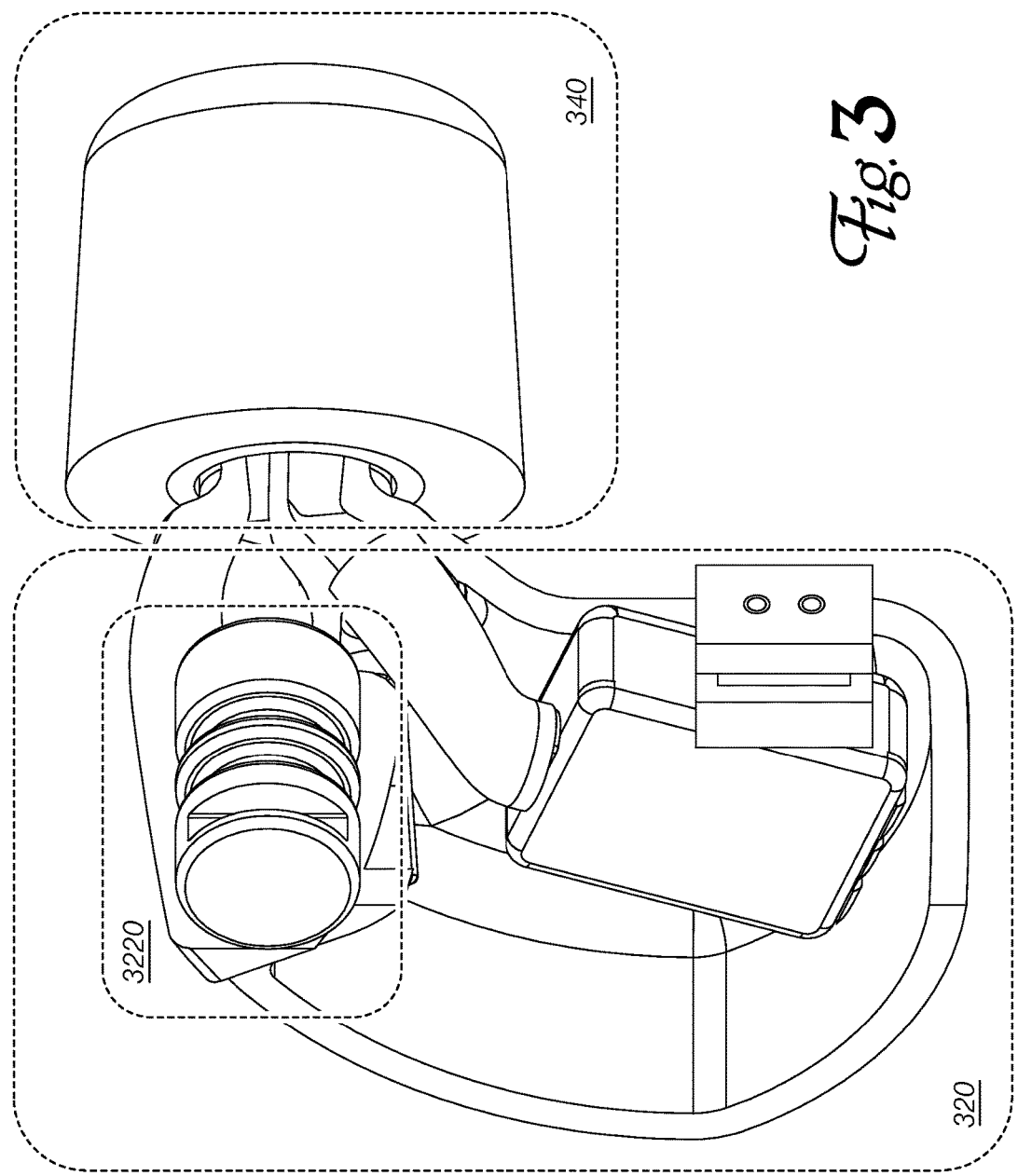
FIG. 3 shows a cutaway view of an embodiment comprising audio drivers.

FIG. 3 shows a partial cutaway view of an in-ear monitor according to an embodiment of the invention. The elements in box 320 correspond to the portion of the embodiment shown at 120 in FIG. 1: they rest in the user's outer ear. Box 340 identifies portions of the embodiment that enter the user's ear canal. Box 3220 indicates the position of a vent module according to an embodiment; this may be the same as the vent module 220 described in reference to FIG. 2.

Figure 4:
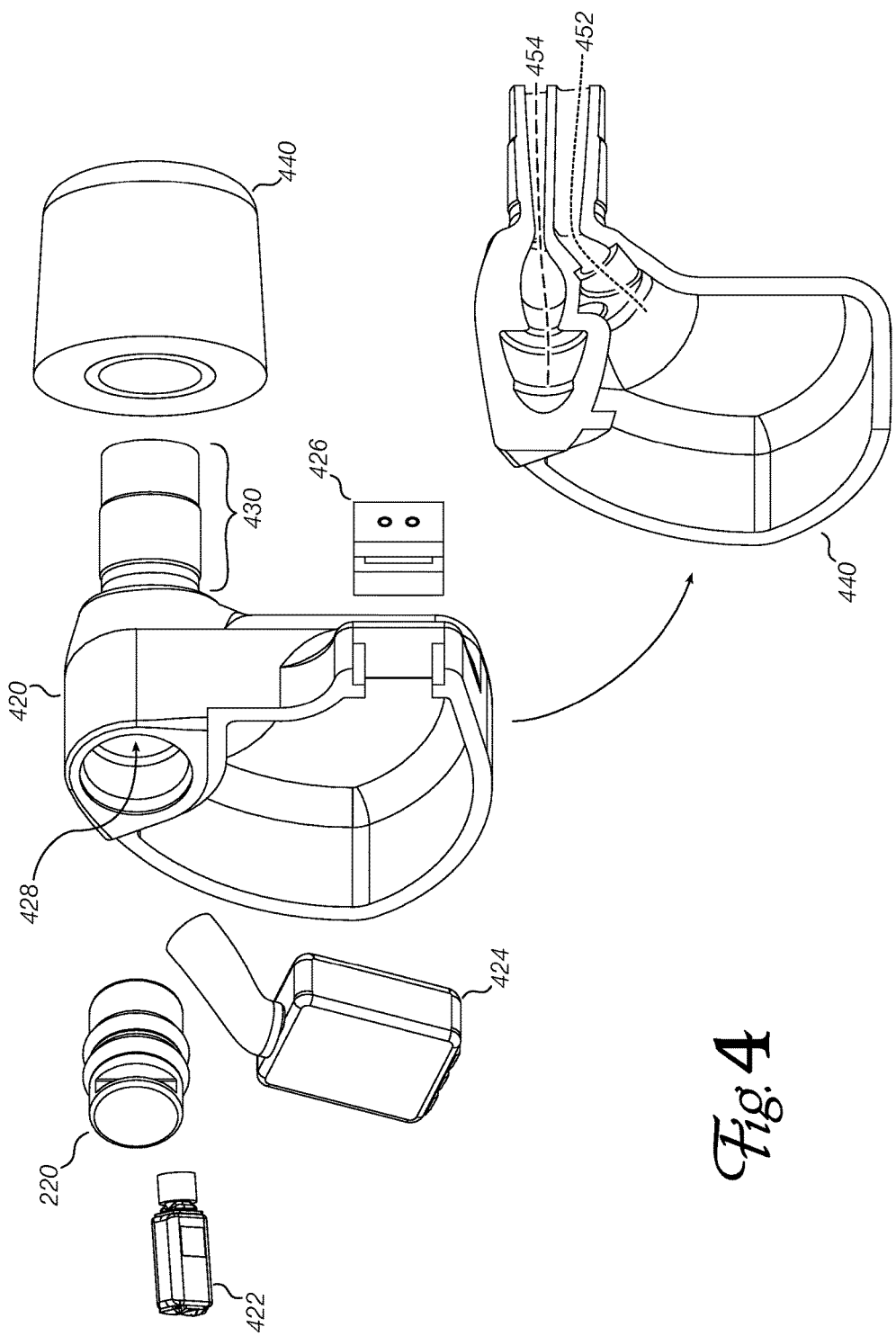
FIG. 4 shows an exploded and cutaway view of an in-ear monitor according to an embodiment.

FIG. 4 shows an exploded view of the in-ear monitor of FIG. 3. 420 is a housing that holds high and low-frequency audio drivers 422, 424. 426 is an electrical interface that accepts signals for the drivers. Acoustically-tuned vent module 220 may be inserted into socket 428, where it functions similarly to what has been described above. Stem 430 extends into the user's ear canal. When assembled, soft, conforming foam plug 440 surrounds stem 430 and seals the ear canal. In a custom-fitted embodiment, housing 420 (and its internal components) may be enclosed or embedded into a polymer mass that has been cast from a mold of the user's outer ear and ear canal.

Cutaway 450 shows two separate channels in housing 420: 452 carries audio waves from drivers 422 and 424 through stem 430 and into the sealed portion of the ear canal (see FIG. 1 at 150). 454 connects vent-module socket 428 to the same sealed portion. Channels 452 and 454 may be separate all the way through housing 420 and stem 430, or they may merge within the stem to form a combined single channel connecting to the sealed portion. (The choice between fully separate channels or partly merged channels is a design decision driven by manufacturability and audio performance considerations.)

Figure 5:
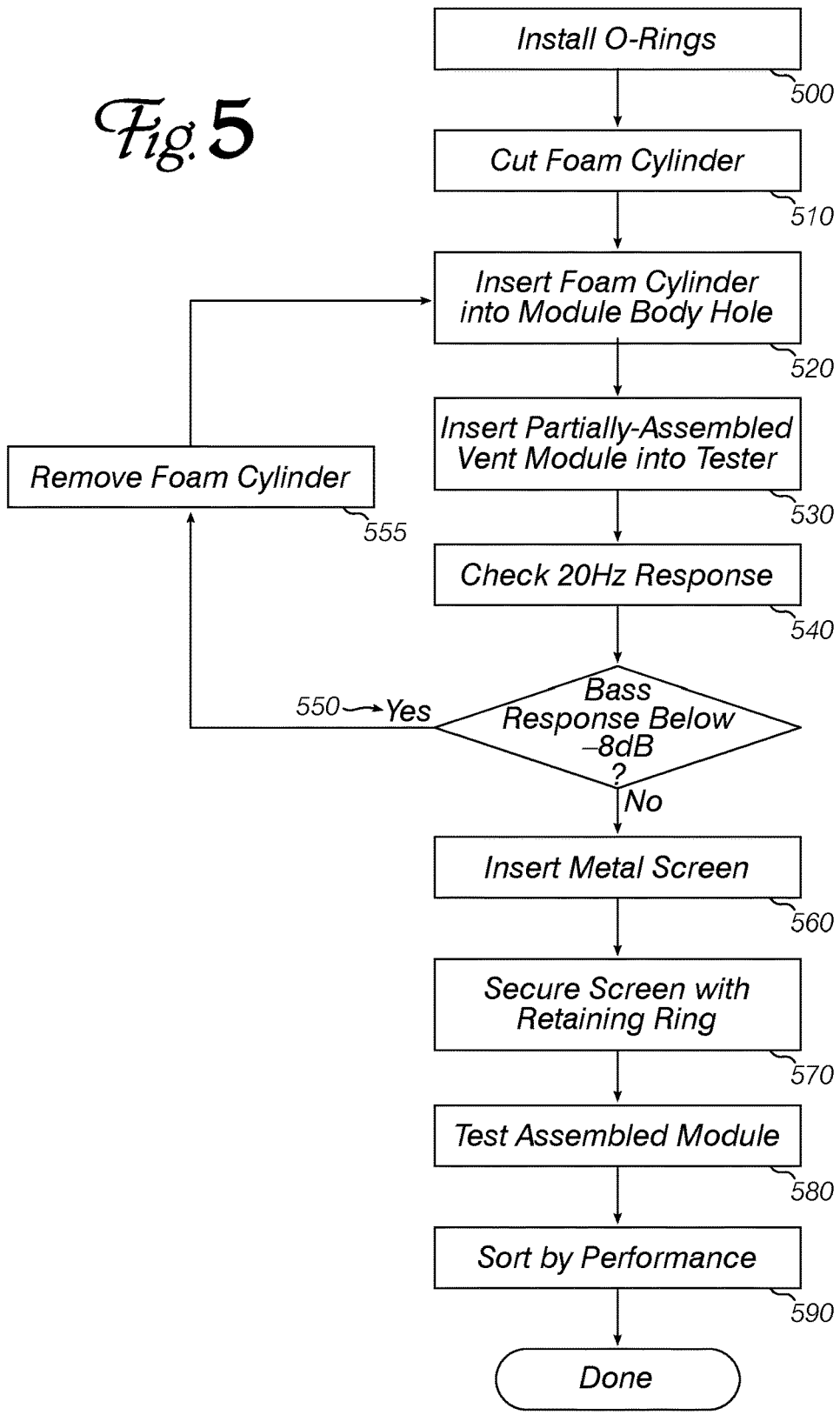
FIG. 5 outlines a manufacturing process for components of an embodiment.

FIG. 5 is a flow chart outlining a method for assembling and tuning a vent module according to an embodiment of the invention. Using plastic, non-marking tweezers, install O-rings into the grooves of a vent module body (500). Cut a section of open-cell viscoelastic foam from a spool of suitable diameter stock (510). The exact length required depends on the characteristics of the foam; commercially-available foams vary slightly from their nominal values. The typical length is usually in the range from 2.5 mm to 2.7 mm, depending on foam porosity. This step produces a small cylindrical section of foam.

A preferred foam stock material is an extruded round material having a protective sheath or skin on its outer surface. This skin protects the foam and improves its dimensional (circumferential) uniformity.

Insert the foam cylinder into the module body, making sure that it is fully seated in the corresponding hole in the vent module body (520). Inspect the foam carefully to ensure that the outer surface of the cylinder is not wrinkled—it should be in full contact with the inner wall of the module body. If there are any folds, wrinkles or other imperfections, remove and re-insert the cylinder.

Insert the partially-assembled vent module into the socket of a testing assembly (530). Using a pink noise source and frequency analysis software, check the bass frequency response of the module (540), paying particular attention to the attenuation at 20 Hz. Module performance is specified (by convention) as the attenuation at this frequency. The testing procedure checks attenuation at other frequencies as well, and modules are expected to exhibit a response within ±1 dB of nominal or target levels across the tested range. Remove the module from the tester.

If the bass response was below −8 dB (550), remove the foam (555) and reinsert it (520). (If removal and reinsertion has been attempted three times without improvement, the foam cylinder should be discarded and the process restarted at 510.)

Insert a metal mesh screen into the vent module (560) and secure it in place using a Delrin® retaining ring (570).

Perform a final testing sequence on the fully-assembled module (580) and place it with others of similar performance (e.g., "Low," "Normal" or "High" bass) (590).

The applications of the present invention have been described largely by reference to specific examples and in terms of particular choices of materials, configurations and assemblies. However, those of skill in the art will recognize that audio-level-neutral attenuation and pressure venting can also be produced by materials, structures and assemblies that are different from the examples herein described. Such alternate implementations are understood to be captured according to the following claims.

We claim:

1. An earpiece comprising:
a body configured to rest in an outer ear of a wearer;
a stem coupled to the body, said stem configured to extend into an ear canal of the wearer and to seal the ear canal;
a vent connecting an airspace inside the sealed ear canal to an ambient atmosphere outside the body; and
a pressure-management material removably fixed within the vent to control passage of air through the vent, wherein
the pressure-management material provides a targeted audio response and permits pressure equalization between the airspace inside the sealed air canal and the ambient atmosphere over an insertion time of the earpiece.

2. The earpiece of claim 1, further comprising:
a discrete module removably secured within the vent, said discrete module containing the pressure-management material.

3. The earpiece of claim 2 wherein:
the discrete module is a cylinder,
the vent comprises a cylindrical portion, and wherein
a diameter of the cylinder is approximately equal to a diameter of the cylindrical portion.

4. The earpiece of claim 3 wherein the discrete module comprises:
means for preventing air from passing through the vent between an outer surface of the discrete module and an inner surface of the cylindrical portion of the vent.

5. The earpiece of claim 3 wherein the discrete module comprises:
a blind hole along an axis of the cylinder, said blind hole containing the pressure-management material; and
a vent orifice connecting the blind hole to an outer surface of the discrete module at a location of the outer surface that is outside the cylindrical portion of the vent when the discrete module is fully engaged in the cylindrical portion of the vent.

6. The earpiece of claim 3 wherein the discrete module comprises:
opposing slots formed in an outer surface of the discrete module near one end thereof, said opposing slots exposed outside the cylindrical portion of the vent when the discrete module is fully engaged in the cylindrical portion of the vent.

7. The earpiece of claim 3 wherein the discrete module comprises:
a porous mesh screen near one end of the discrete module, said screen to prevent the pressure-management material from escaping from the discrete module.

8. The earpiece of claim 1 wherein the pressure-management material is a viscoelastic open-cell foam.

9. The earpiece of claim 8 wherein the viscoelastic open-cell foam is a cylindrical segment of viscoelastic open-cell foam having a protective skin around its circumference.

10. An earpiece comprising:
a body shaped to match an impression of a wearer's outer ear and adjacent outer ear canal, the body having a vent extending directly from an orifice within the wearer's ear canal to an ambient atmosphere outside the wearer's outer ear;
at least one audio driver to emit sound waves into the wearer's outer ear canal through an audio passage; and
a discrete carrier for an open-cell viscoelastic foam removably secured within the vent, wherein
the open-cell viscoelastic foam is fixed within the discrete carrier to control passage of air through the vent.

11. The earpiece of claim 10 wherein the audio passage is separate from the vent.

12. The earpiece of claim 10 wherein said discrete carrier is adapted to occlude the vent so that air can only pass through the open-cell viscoelastic foam in the discrete carrier when traveling through the vent.

13. The earpiece of claim 12 wherein the discrete carrier is a rigid cylinder.

14. The earpiece of claim 13 wherein the rigid cylinder comprises at least one sealing O ring.

15. The earpiece of claim 13 wherein an air passage is formed within the rigid cylinder comprises an air passage, said air passage having at least one change of direction.

16. The earpiece of claim 15 wherein the air passage has at least one right-angle bend.

17. A method comprising:
inserting a pressure-management material into a vent module;
measuring sound transmission levels at a plurality of different frequencies from a source, through the vent module containing the pressure-management material, to a sink; and
if a first sound transmission level at a first frequency differs from a second sound transmission level at a second frequency by more than a predetermined amount,
adjusting the pressure-management material within the vent module before repeating the measuring operation to produce an acoustically tuned vent module; and
inserting the acoustically tuned vent module containing the pressure management material into an earpiece.

18. The method of claim 17 wherein the pressure-management material is an open-cell viscoelastic foam.

19. The method of claim 17, further comprising:
sorting a plurality of assembled vent modules into performance bins by the sound transmission level of each of the assembled vent modules at a predetermined frequency.

* * * * *